US008234000B2

(12) United States Patent
Andersson et al.

(10) Patent No.: US 8,234,000 B2
(45) Date of Patent: Jul. 31, 2012

(54) METHOD AND APPARATUS FOR OBTAINING DATA FOR A DENTAL COMPONENT AND A PHYSICAL DENTAL MODEL

(75) Inventors: Matts Andersson, Lerum (SE); Jenny Fäldt, Mölndal (SE); Per-Olof Karlsson, Alingsas (SE)

(73) Assignee: Nobel Biocare Services AG, Zurich-Flughafen (CH)

( * ) Notice: Subject to any disclaimer, the term of this patent is extended or adjusted under 35 U.S.C. 154(b) by 280 days.

(21) Appl. No.: 12/447,467

(22) PCT Filed: Jan. 8, 2007

(86) PCT No.: PCT/SE2007/000011
§ 371 (c)(1),
(2), (4) Date: Jun. 24, 2009

(87) PCT Pub. No.: WO2008/051130
PCT Pub. Date: May 2, 2008

(65) Prior Publication Data
US 2010/0106275 A1   Apr. 29, 2010

(30) Foreign Application Priority Data

Oct. 27, 2006   (SE) .................................. 0602271-9

(51) Int. Cl.
*G06F 19/00* (2006.01)
*G06F 17/10* (2006.01)
*G06G 7/48* (2006.01)
(52) U.S. Cl. ....................... 700/98; 703/2; 703/6; 703/7
(58) Field of Classification Search .................... 700/98; 703/2, 6, 7; 433/213, 214
See application file for complete search history.

(56) References Cited

U.S. PATENT DOCUMENTS
1,798,518 A   3/1931   Bennet
(Continued)

FOREIGN PATENT DOCUMENTS
DE            602015            8/1934
(Continued)

OTHER PUBLICATIONS

Written Opinion of the International Searching Authority for International application No. PCT/SE2007/000011, mailed on Jul. 12, 2007, in 5 pages.

(Continued)

*Primary Examiner* — Kakali Chaki
*Assistant Examiner* — Sivalingam Sivanesan
(74) *Attorney, Agent, or Firm* — Knobbe, Martens, Olson & Bear, LLP.

(57) ABSTRACT

Methods for obtaining data and for manufacturing a dental component and a physical dental model of at least a part of a dental structure are provided which can improve processing times and provide sufficient manufacturing accuracy. An embodiment of the method can comprise obtaining a first data record for manufacturing the dental component and a second data record for manufacturing the physical dental model. The first data record can comprise data based on a portion of a digital dental model. The second data record can comprise data based on at least the portion of the digital dental model. In this regard, the data upon which the first and second data records are based can be obtained using first and second scanning resolutions in order to improve processing times and provide sufficient accuracy.

16 Claims, 9 Drawing Sheets

U.S. PATENT DOCUMENTS

| | | | |
|---|---|---|---|
| 4,252,523 A | 2/1981 | Gayso | |
| 4,854,868 A | 8/1989 | Pitre | |
| 5,052,928 A | 10/1991 | Andersson | |
| 5,059,758 A | 10/1991 | Andersson | |
| 5,069,622 A | 12/1991 | Rangert et al. | |
| 5,076,785 A | 12/1991 | Tsai | |
| 5,192,173 A | 3/1993 | Andersson et al. | |
| 5,192,472 A | 3/1993 | Andersson | |
| 5,382,164 A | 1/1995 | Stern | |
| 5,440,496 A | 8/1995 | Andersson et al. | |
| 5,497,336 A | 3/1996 | Andersson et al. | |
| 5,549,476 A | 8/1996 | Stern | |
| 5,565,152 A | 10/1996 | Odén et al. | |
| 5,587,912 A | 12/1996 | Andersson et al. | |
| 5,607,305 A | 3/1997 | Andersson et al. | |
| 5,652,709 A | 7/1997 | Andersson et al. | |
| 5,690,490 A | 11/1997 | Cannon et al. | |
| 5,733,126 A | 3/1998 | Andersson et al. | |
| 5,752,826 A | 5/1998 | Andreiko | |
| 5,752,828 A | 5/1998 | Andersson et al. | |
| 5,800,174 A | 9/1998 | Andersson | |
| 5,851,115 A | 12/1998 | Carlsson et al. | |
| 5,880,962 A | 3/1999 | Andersson et al. | |
| 5,938,446 A | 8/1999 | Andersson et al. | |
| 5,975,893 A | 11/1999 | Chishti et al. | |
| 6,062,861 A | 5/2000 | Andersson | |
| 6,099,314 A | 8/2000 | Kopelman et al. | |
| 6,212,442 B1 | 4/2001 | Andersson et al. | |
| 6,217,325 B1 | 4/2001 | Chishti et al. | |
| 6,217,334 B1 | 4/2001 | Hultgren | |
| 6,227,850 B1 | 5/2001 | Chishti et al. | |
| 6,261,098 B1 | 7/2001 | Persson | |
| 6,318,994 B1 | 11/2001 | Chishti et al. | |
| 6,364,660 B1 * | 4/2002 | Durbin et al. | 433/29 |
| 6,371,761 B1 | 4/2002 | Cheang et al. | |
| 6,386,878 B1 | 5/2002 | Pavlovskaia et al. | |
| 6,398,548 B1 | 6/2002 | Muhammad et al. | |
| 6,406,292 B1 | 6/2002 | Chishti et al. | |
| 6,413,085 B1 | 7/2002 | Lee | |
| 6,450,807 B1 | 9/2002 | Chishti et al. | |
| 6,457,972 B1 | 10/2002 | Chishti et al. | |
| 6,463,344 B1 | 10/2002 | Pavloskaia et al. | |
| 6,471,511 B1 | 10/2002 | Chishti et al. | |
| 6,511,318 B2 | 1/2003 | Kim | |
| 6,554,611 B2 | 4/2003 | Chishti et al. | |
| 6,558,162 B1 | 5/2003 | Porter et al. | |
| 6,582,229 B1 | 6/2003 | Miller et al. | |
| 6,602,070 B2 | 8/2003 | Miller et al. | |
| 6,607,386 B1 | 8/2003 | Andersson et al. | |
| 6,626,666 B2 | 9/2003 | Chishti et al. | |
| 6,629,840 B2 | 10/2003 | Chishti et al. | |
| 6,633,789 B1 | 10/2003 | Nikolskiy et al. | |
| 6,640,150 B1 | 10/2003 | Persson et al. | |
| 6,665,570 B2 | 12/2003 | Pavloskaia et al. | |
| 6,682,346 B2 | 1/2004 | Chishti et al. | |
| 6,685,469 B2 | 2/2004 | Chishti et al. | |
| 6,688,886 B2 | 2/2004 | Hughes et al. | |
| 6,697,164 B1 | 2/2004 | Babayoff et al. | |
| 6,699,037 B2 | 3/2004 | Chishti et al. | |
| 6,705,863 B2 | 3/2004 | Phan et al. | |
| 6,722,880 B2 | 4/2004 | Chishti et al. | |
| 6,729,876 B2 | 5/2004 | Chishti et al. | |
| 6,767,208 B2 | 7/2004 | Kaza | |
| 6,783,360 B2 | 8/2004 | Chishti | |
| 6,786,721 B2 | 9/2004 | Chishti et al. | |
| 6,790,040 B2 | 9/2004 | Amber et al. | |
| 6,802,713 B1 | 10/2004 | Chishti et al. | |
| 6,821,123 B2 | 11/2004 | Andersson et al. | |
| 6,940,611 B2 | 9/2005 | Babayoff et al. | |
| 6,948,936 B2 | 9/2005 | Miller et al. | |
| 6,979,196 B2 | 12/2005 | Nikolskiy et al. | |
| 7,030,383 B2 | 4/2006 | Babayoff et al. | |
| 7,040,896 B2 | 5/2006 | Pavlovskaia et al. | |
| 7,059,850 B1 | 6/2006 | Phan et al. | |
| 7,074,038 B1 | 7/2006 | Miller | |
| 7,089,070 B2 | 8/2006 | Andersson et al. | |
| 7,092,107 B2 | 8/2006 | Babayoff et al. | |
| 7,092,780 B2 | 8/2006 | Ganley et al. | |
| 7,092,784 B1 | 8/2006 | Simkins | |
| 7,134,874 B2 | 11/2006 | Chishti et al. | |
| 7,140,877 B2 | 11/2006 | Kaza | |
| 7,142,312 B2 | 11/2006 | Quadling et al. | |
| 7,156,661 B2 | 1/2007 | Choi et al. | |
| 7,175,435 B2 | 2/2007 | Andersson et al. | |
| 7,202,466 B2 | 4/2007 | Babayoff et al. | |
| 7,214,946 B2 | 5/2007 | Babayoff et al. | |
| 7,220,122 B2 | 5/2007 | Chishti | |
| 7,220,124 B2 | 5/2007 | Taub et al. | |
| 7,230,725 B2 | 6/2007 | Babayoff et al. | |
| 7,241,142 B2 | 7/2007 | Abolfathi et al. | |
| 7,255,558 B2 | 8/2007 | Babayoff et al. | |
| 7,273,367 B2 | 9/2007 | Hughes et al. | |
| 7,286,954 B2 | 10/2007 | Kopelman et al. | |
| 7,319,529 B2 | 1/2008 | Babayoff | |
| 7,320,592 B2 | 1/2008 | Chishti et al. | |
| 7,326,051 B2 | 2/2008 | Miller | |
| 7,331,783 B2 | 2/2008 | Chishti et al. | |
| 7,333,874 B2 | 2/2008 | Taub et al. | |
| 7,357,634 B2 | 4/2008 | Knopp | |
| 7,361,020 B2 | 4/2008 | Abolfathi et al. | |
| 7,363,239 B1 | 4/2008 | Andersson et al. | |
| 7,373,286 B2 * | 5/2008 | Nikolskiy et al. | 703/7 |
| 7,377,778 B2 | 5/2008 | Chishti et al. | |
| 7,425,131 B2 | 9/2008 | Amber et al. | |
| 7,428,481 B2 | 9/2008 | Nikolskiy et al. | |
| 7,433,810 B2 | 10/2008 | Pavloskaia et al. | |
| 7,435,083 B2 | 10/2008 | Chishti et al. | |
| 7,442,040 B2 | 10/2008 | Kuo | |
| 7,452,207 B2 | 11/2008 | Miller et al. | |
| 7,474,307 B2 | 1/2009 | Chishti et al. | |
| 7,476,100 B2 | 1/2009 | Kuo | |
| 7,477,402 B2 | 1/2009 | Babayoff et al. | |
| 7,511,829 B2 | 3/2009 | Babayoff | |
| 7,536,234 B2 | 5/2009 | Kopelman et al. | |
| 7,547,873 B2 | 6/2009 | Babayoff et al. | |
| 7,555,403 B2 | 6/2009 | Kopelman et al. | |
| 2001/0002310 A1 | 5/2001 | Chishti et al. | |
| 2001/0006770 A1 | 7/2001 | Chishti et al. | |
| 2001/0008751 A1 | 7/2001 | Chishti et al. | |
| 2001/0009753 A1 | 7/2001 | Chishti et al. | |
| 2002/0064747 A1 | 5/2002 | Chishti et al. | |
| 2002/0064748 A1 | 5/2002 | Chishti et al. | |
| 2002/0064759 A1 * | 5/2002 | Durbin et al. | 433/213 |
| 2002/0119423 A1 | 8/2002 | Chishti et al. | |
| 2002/0150855 A1 | 10/2002 | Shishti et al. | |
| 2002/0177108 A1 | 11/2002 | Pavlovskaia et al. | |
| 2003/0003416 A1 | 1/2003 | Chishti et al. | |
| 2003/0008259 A1 | 1/2003 | Kuo et al. | |
| 2003/0009252 A1 | 1/2003 | Pavlovskaia et al. | |
| 2003/0064345 A1 | 4/2003 | Chishti et al. | |
| 2003/0139834 A1 | 7/2003 | Nikolskiy et al. | |
| 2003/0198917 A1 | 10/2003 | Miller et al. | |
| 2003/0207227 A1 | 11/2003 | Abolfathi | |
| 2003/0232302 A1 | 12/2003 | Babayoff et al. | |
| 2003/0235803 A1 | 12/2003 | Nikolskiy et al. | |
| 2004/0023183 A1 | 2/2004 | Miller et al. | |
| 2004/0023188 A1 | 2/2004 | Pavlovskaia et al. | |
| 2004/0090638 A1 | 5/2004 | Babayoff et al. | |
| 2004/0096799 A1 | 5/2004 | Hughes et al. | |
| 2004/0110110 A1 | 6/2004 | Chishti et al. | |
| 2004/0128010 A1 | 7/2004 | Pavlovskaia et al. | |
| 2004/0137400 A1 | 7/2004 | Chishti et al. | |
| 2004/0166456 A1 | 8/2004 | Chishti et al. | |
| 2004/0170943 A1 | 9/2004 | Chishti et al. | |
| 2004/0175671 A1 | 9/2004 | Jones et al. | |
| 2004/0191719 A1 | 9/2004 | Kaza | |
| 2004/0204787 A1 * | 10/2004 | Kopelman et al. | 700/182 |
| 2004/0219490 A1 * | 11/2004 | Gartner et al. | 433/218 |
| 2004/0243361 A1 | 12/2004 | Steuben et al. | |
| 2004/0259051 A1 | 12/2004 | Brajnovic | |
| 2005/0019721 A1 | 1/2005 | Chishti | |
| 2005/0026102 A1 | 2/2005 | Miller | |
| 2005/0048432 A1 | 3/2005 | Choi et al. | |
| 2005/0055118 A1 | 3/2005 | Nikolskiy et al. | |
| 2005/0079468 A1 | 4/2005 | Chishti et al. | |
| 2005/0106528 A1 | 5/2005 | Abolfathi et al. | |
| 2005/0106529 A1 | 5/2005 | Abolfathi et al. | |

| | | | | | | |
|---|---|---|---|---|---|---|
| 2005/0177261 A1* | 8/2005 | Durbin et al. ............ 700/98 | | 2008/0085487 A1 | 4/2008 | Kuo et al. |
| 2005/0186524 A1 | 8/2005 | Abolfathi et al. | | 2008/0090211 A1 | 4/2008 | Andersson |
| 2005/0191593 A1 | 9/2005 | Knopp | | 2008/0131832 A1 | 6/2008 | Miller |
| 2005/0192835 A1 | 9/2005 | Kuo et al. | | 2008/0131841 A1 | 6/2008 | Taub et al. |
| 2005/0196724 A1 | 9/2005 | Miller et al. | | 2008/0166676 A1 | 7/2008 | Chishti et al. |
| 2005/0208449 A1 | 9/2005 | Abolfathi et al. | | 2008/0182220 A1 | 7/2008 | Chishti et al. |
| 2005/0244782 A1 | 11/2005 | Chishti et al. | | 2008/0182221 A1 | 7/2008 | Chishti et al. |
| 2005/0264828 A1 | 12/2005 | Babayoff et al. | | 2008/0187879 A1 | 8/2008 | Chishti et al. |
| 2005/0277091 A1 | 12/2005 | Andersson et al. | | 2008/0193899 A1 | 8/2008 | Karlsson et al. |
| 2006/0008777 A1 | 1/2006 | Peterson et al. | | 2008/0206710 A1 | 8/2008 | Kruth et al. |
| 2006/0040236 A1* | 2/2006 | Schmitt ............ 433/213 | | 2008/0206714 A1 | 8/2008 | Schmitt |
| 2006/0068355 A1 | 3/2006 | Schultz | | 2008/0248443 A1 | 10/2008 | Chishti et al. |
| 2006/0093987 A1 | 5/2006 | Wen | | 2008/0259411 A1 | 10/2008 | Karlsson |
| 2006/0093993 A1 | 5/2006 | Wen | | 2008/0261176 A1 | 10/2008 | Hurson |
| 2006/0097178 A1 | 5/2006 | Babayoff et al. | | 2008/0268400 A1 | 10/2008 | Moss et al. |
| 2006/0106484 A1 | 5/2006 | Saliger et al. | | 2008/0288289 A1 | 11/2008 | Sah |
| 2006/0158665 A1 | 7/2006 | Babayoff et al. | | 2008/0300716 A1 | 12/2008 | Kopelman et al. |
| 2006/0212260 A1 | 9/2006 | Kopelman et al. | | 2008/0305452 A1 | 12/2008 | Sterental et al. |
| 2006/0263738 A1 | 11/2006 | Kuo | | 2008/0305453 A1 | 12/2008 | Kitching et al. |
| 2006/0286501 A1 | 12/2006 | Chishti et al. | | 2008/0306724 A1 | 12/2008 | Kitching et al. |
| 2007/0003907 A1 | 1/2007 | Chishti et al. | | 2008/0316209 A1 | 12/2008 | Wen |
| 2007/0026363 A1 | 2/2007 | Lehmann et al. | | 2009/0148807 A1 | 6/2009 | Babayoff et al. |
| 2007/0031774 A1 | 2/2007 | Cinader, Jr. et al. | | 2009/0148809 A1 | 6/2009 | Kuo et al. |
| 2007/0077537 A1 | 4/2007 | Taub et al. | | 2009/0153858 A1 | 6/2009 | Babayoff |
| 2007/0087302 A1 | 4/2007 | Reising et al. | | 2009/0153879 A1 | 6/2009 | Babayoff et al. |
| 2007/0092850 A1 | 4/2007 | Kaza | | 2009/0304302 A1 | 12/2009 | Kordass et al. |
| 2007/0092854 A1 | 4/2007 | Powell et al. | | | | |
| 2007/0109559 A1 | 5/2007 | Babayoff et al. | | | | |

FOREIGN PATENT DOCUMENTS

| | | |
|---|---|---|
| DE | 10061088 | 6/2002 |
| EP | 1568335 | 8/2005 |
| EP | 1957005 A2 | 8/2008 |
| FR | 1438237 | 4/1966 |
| JP | 2006-21024 | 1/2006 |
| SE | 441333 | 9/1985 |
| WO | WO 2006/013074 | 2/2006 |
| WO | WO 2007/062658 A2 | 6/2007 |
| WO | WO 2008/051141 A1 | 5/2008 |
| WO | WO 2008/051142 A1 | 5/2008 |

| | | |
|---|---|---|
| 2007/0128573 A1 | 6/2007 | Kuo |
| 2007/0128574 A1 | 6/2007 | Kuo et al. |
| 2007/0129991 A1 | 6/2007 | Kuo |
| 2007/0134613 A1 | 6/2007 | Kuo et al. |
| 2007/0134617 A1 | 6/2007 | Babayoff et al. |
| 2007/0141525 A1 | 6/2007 | Cinader, Jr. |
| 2007/0141527 A1 | 6/2007 | Kuo et al. |
| 2007/0145248 A1 | 6/2007 | Babayoff et al. |
| 2007/0164203 A1 | 7/2007 | Babayoff et al. |
| 2007/0168152 A1 | 7/2007 | Matov et al. |
| 2007/0203663 A1 | 8/2007 | Kopelman et al. |
| 2007/0238065 A1 | 10/2007 | Sherwood et al. |
| 2007/0243503 A1 | 10/2007 | Gagnon et al. |
| 2007/0281284 A1 | 12/2007 | Andersson et al. |
| 2007/0292004 A1 | 12/2007 | Peters |
| 2007/0293748 A1 | 12/2007 | Engvall et al. |
| 2008/0024768 A1 | 1/2008 | Babayoff |
| 2008/0038688 A1 | 2/2008 | Kopelman et al. |
| 2008/0038692 A1 | 2/2008 | Andersson et al. |
| 2008/0044786 A1 | 2/2008 | Kalili |
| 2008/0070181 A1 | 3/2008 | Abolfathi et al. |

OTHER PUBLICATIONS

International Preliminary Report on Patentability for International application No. PCT/SE2007/000011, issued on Apr. 28, 2009, in 6 pages.

International Search Report received in corresponding PCT Application No. PCT/SE2007/000011, mailed Jul. 12, 2007, 6 pages.

* cited by examiner

METHOD AND APPARATUS FOR OBTAINING DATA FOR A DENTAL COMPONENT AND A PHYSICAL DENTAL MODEL

CROSS-REFERENCE TO RELATED APPLICATIONS

This application is a national stage application under 35 U.S.C. §371 of PCT Application No. PCT/SE2007/000011 designating the United States, filed on Jan. 8, 2007. The PCT Application was published in English as WO 2008/051130 A1 on May 2, 2008 and claims the benefit of the earlier filing date of Swedish Patent Application No. 0602271-9, filed Oct. 27, 2006. The contents of PCT Application No. PCT/SE2007/000011, including publication WO 2008/051130 A1, and Swedish Patent Application No. 0602271-9, are incorporated herein by reference in their entirety.

BACKGROUND

1. Field of the Inventions

The present inventions relate to a method, a system and a computer program product for obtaining data for manufacturing a dental component and a physical dental model.

2. Description of Related Art

A dental restoration, such as a dental bridge, a crown, an onlay, or an inlay, can be prefabricated before it is installed into a patient. The dental restoration may be manually fabricated, e.g., by a dental technician, or manufactured using a CAD/CAM (Computer Aided Design/Computed Aided Manufacturing) procedure. One such CAD/CAM procedure, which includes various products and procedures, is provided within the Procera® concept by Nobel Biocare®. The dental restoration may be built up by a dental component forming a framework, such as a ceramic coping, and a veneering layer. The veneering layer may be formed with porcelain. The CAD/CAM procedure may be used to only manufacture the dental component, or the entire dental restoration.

Irrespectively whether the dental restoration is finalized manually or by means of the CAD/CAM procedure, the following steps are normally carried out. First, providing a preparation by preparing one or several teeth to be restored; next, taking an impression of at least one of the upper jaw and the lower jaw of a patient, which includes the preparation; casting based on the impression to provide a study cast of at least a portion of the patients dental structure, the preparation, and soft tissue; then, manufacturing the dental component; and finally, fitting and/or adjusting the dental component using the plaster study cast and an articulator to provide the dental restoration. The fitting operation may comprise forming the veneering layer. If the CAD/CAM procedure is utilized to form the veneering layer, a manual fitting operation may comprise grinding the veneering layer to provide accurate occlusion.

To obtain the geometry of the surface of the dental structure, and possibly adjacent soft tissue, of the patient, the impression is taken to form a negative model. A bite index may also be taken to record the spatial relationship of the teeth in the upper jaw and the teeth of the lower jaw of the patient. For the impression-taking process, an impression tray may be used. When the impression material has set, plaster is poured into the impression, whereby the positive model of the dental structure and adjacent soft tissue is provided once the plaster has set.

If the CAD/CAM procedure is used, the plaster study cast can be sectioned, wherein the portion of the study cast containing the model of the preparation is removed from the other portion of the study cast. The model of the preparation can be scanned using a probe scanner or an optical scanner to provide a data record containing information of the geometrical shape of the surface thereof. The data record can be sent to a manufacturing facility for manufacturing of the dental component.

The model of the upper jaw and the model of the lower jaw can be mounted into an articulator to be used during the fitting operation. The bite index can be used to provide a spatial relationship between the models of the upper and lower jaws, which corresponds to the spatial relationship between the teeth of the upper and lower jaw of the patient. When the study cast has been properly mounted in the articulator using the bite index, the fitting operation can commence.

When the veneering layer is added to dental component, the study cast may be used to check the accuracy of the dental component and/or as a die for forming the veneering layer. The study cast may also be used for occlusion fitting and/or checking. During the fitting operation, the dental component is seated on the model of the preparation. The dental component is normally manufactured using a high precision manufacturing procedure. Hence, a close interrelationship between the inner surface of the dental component and the outer surface of the model of the preparation is provided, as the model of the preparation was scanned to generate the data record for the dental component. Accuracy is important in order to, i.e. avoid cracking of the dental restoration after final installation on the preparation.

SUMMARY

According to at least one of the embodiments disclosed herein are the realizations that fabrication of the study cast can be relatively time consuming and cumbersome. It is also inconvenient and sticky to handle the plaster. Furthermore, it can be cumbersome and time consuming to mount the study cast in the articulator. Also, the curing process of plaster can be difficult to control. However, it has been considered necessary to make the plaster models when dental components have to be fitted after CAD production to provide a final restoration. This is, e.g., because the fit against the preparation of the patient and/or against one or several occluding teeth needs to be checked and needs to be accurate. The accuracy is provided because the scanning and the fitting operations are performed using the same model.

U.S. Pat. No. 5,440,496 discloses a CAD/CAM procedure, which describes various techniques for scanning a portion of a plaster study cast, and manufacturing of three-dimensional bodies to form part of an artificial replacement for one or several teeth.

US-A-2005/0177261 discloses a method for treating teeth, without using a plaster model. The method includes capturing a digital dental model taken directly within an oral cavity to generate data representing the digital dental model. A physical dental model is produced using the data representing the digital dental model and a stereolithography apparatus. The physical dental model is then used as a pattern to manually fabricate a crown and for accuracy check. However, in accordance with at least one of the embodiments disclosed herein is the realization that even if the procedure described in US-A-2005/0177261 solves some issues relating to the use of a plaster model, the method does not suggest CAD/CAM production of the crown. In this regard, in accordance with another of the embodiments disclosed herein is the realization that accuracy is provided as the crown is formed directly on the physical dental model.

Accordingly, embodiments of the present inventions preferably seek to mitigate, alleviate or eliminate one or more deficiencies, disadvantages or issues in the art, such as the above-identified, singly or in any combination. For example, some embodiments can provide a method for obtaining data for manufacturing a dental component and a physical dental model. In other embodiments, there is provided a system for obtaining data for manufacturing a dental component and a physical dental model. In yet other embodiments, there is provided a computer program product for executing an embodiment of the method.

According to an aspect of the inventions, a method for obtaining data for manufacturing a dental component and a physical dental model of at least a part of a dental structure is provided. The method comprises obtaining a first data record for manufacturing the dental component. The first data record comprises information based on a portion of a digital dental model. Also, the method comprises obtaining a second data record for manufacturing the physical dental model. The second data record comprises information based on at least the portion of the digital dental model.

According to some embodiments, obtaining the first data record comprises obtaining a data record comprising information based on a preparation portion of the digital dental model. Also, obtaining the second data record comprises obtaining information based on at least the preparation portion of the digital dental model.

According to some embodiments, obtaining the first data record and obtaining the second data record comprise obtaining information of a geometrical shape a surface of at least the portion of the digital dental model.

According to some embodiments, the method comprises obtaining at least one digital impression of a portion of a physical impression by controlling a scanner device. The portion of the physical impression comprises an impression of a portion of the dental structure. The digital dental model is generated based on the digital impression.

According to some embodiments, obtaining at least one digital impression comprises controlling the scanner device to apply a first scanning resolution when a first portion of the physical impression is scanned. A second scanning resolution is applied when a second portion of the physical impression is scanned. The first scanning resolution is higher than the second scanning resolution.

According to some embodiments, obtaining the second record comprises adding a connection interface to at least a portion of the digital dental model.

According to some embodiments, obtaining the first data record comprises obtaining a data record comprising information, which is based on the portion of the digital dental model. The portion has been generated using a first scanning resolution. Obtaining the second data record comprises obtaining a data record comprising information, which is based at on least the portion of the digital dental model. The portion has been generated using a second scanning resolution. The second scanning resolution is lower than the first scanning resolution. According to some embodiments, obtaining the first data record comprises receiving the first data record at a CAM apparatus, and manufacturing at least the dental component based on the first data record. According to some embodiments, obtaining the second data record comprises receiving the second data record at a free form fabrication apparatus. Also, the method comprises manufacturing the physical dental model based on the second data record.

According to another aspect, a computer program product comprises computer program code means for executing the method for obtaining data for manufacturing a dental component and a physical dental model of at least a part of a dental structure when said computer program code means are run by an electronic device having computer capabilities.

According to another aspect, a system for obtaining data for manufacturing a dental component and a physical dental model of at least a part of a dental structure is provided. The system comprises a data record generating unit adapted to obtain a first data record for manufacturing the dental component. The first data record comprises information based on a portion of a digital dental model. Also, the system is adapted to obtain a second data record for manufacturing the physical dental model. The second data record comprises information based on at least the portion of the digital dental model.

According to some embodiments, the data record generating unit is adapted to obtain for the first data record a data record comprising information based on a preparation portion of the digital dental model. Also, the data record generating unit is adapted to obtain for the second data record information based on at least the preparation portion of the digital dental model. According to some embodiments, the data record generating unit is adapted to obtain for the first data record and the second data record information of a geometrical shape a surface of at least the portion of the digital dental model.

According to some embodiments, the data record generating unit is adapted to obtaining at least one digital impression of a portion of a physical impression by controlling a scanner device. The first portion of the physical impression comprises an impression of a portion of the dental structure. Also, the data record generating unit is adapted to generate the digital dental model based on the digital impression.

According to some embodiments, the data record generating unit is adapted to control the scanner device to apply a first scanning resolution when a first portion of the physical impression is scanned and to apply a second scanning resolution when a second portion of the physical impression is scanned. The first scanning resolution is higher than the second scanning resolution.

According to some embodiments, the data record generating unit is adapted to add a connection interface to at least a portion of the digital dental model.

According to some embodiments, the data record generating unit is adapted to obtain for the first data record a data record comprising information, which is based on the portion of the digital dental model. The portion has been generated using a first scanning resolution. Also, the data record generating unit is adapted to obtain for the second data record a data record comprising information, which is based at on least the portion of the digital dental model. The portion has been generated using a second scanning resolution. The second scanning resolution is lower than the first scanning resolution. According to some embodiments, the system comprises a CAM apparatus adapted to receive the first data record. Also, the CAM apparatus is adapted to manufacture at least the dental component based on the first data record.

According to some embodiments, the system comprises a free form fabrication apparatus adapted to receive the second data record. Also, the free form fabrication apparatus is adapted to manufacture at least the physical dental model based on the second data record.

According to another aspect, a data storage device comprises at least one of the first data record and the second data record.

Further embodiments of the inventions are defined in the dependent claims.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

The abovementioned and other features of the inventions disclosed herein are described below with reference to the drawings of the preferred embodiments. The illustrated embodiments are intended to illustrate, but not to limit the inventions. The drawings contain the following figures.

DETAILED DESCRIPTION OF EMBODIMENTS

Embodiments of the inventions relate to a system, a method, and one or several apparatuses for manufacturing at least a dental component and a physical dental model 80 (FIG. 8b) of at least a part of a dental structure (FIG. 3a) of a patient. The dental structure may comprise one tooth, several teeth, and/or soft tissue of an oral cavity of a patient. The dental component may comprise, e.g., a framework, such as a coping for a crown or a bridge, manufactured by a CAM procedure. A veneering layer, e.g., porcelain, may be manually added to the dental component to provide a final dental restoration, such as the crown or the bridge. Alternatively, the final dental restoration is manufactured by the CAM procedure. Hence, the dental component may be a final bridge or crown, which comprises a framework and a veneering layer added thereon by the CAM procedure.

Embodiments of the inventions also provide for manufacturing of at least a customized dental component using high accuracy CAM production and subsequent fitting on the physical dental model 80. The physical dental model 80 as well as the dental component may be manufactured based on data records. The data records may be obtained from scanning data. The scanning data may be obtained from an impression of at least a portion of the dental structure of the patient. The portion may be at least a portion of a preparation, on which the dental component should be installed.

One of the advantages associated with embodiments disclosed herein is that such embodiments can eliminate the need of making a plaster study cast. Hence, the efficiency of the system according to some embodiments compared to systems using CAD/CAM procedures with a plaster study cast and/or systems involving manual manufacturing of the dental component is improved. Furthermore, the data record for the dental component and the data record for the physical dental model 80 have the same origin. The origin may be a digital dental model 50 (FIG. 5), obtained from the physical impression of the dental structure of the patient. Thus, accuracy between the physical dental model 80 and the dental component is also provided for.

Figure 1:
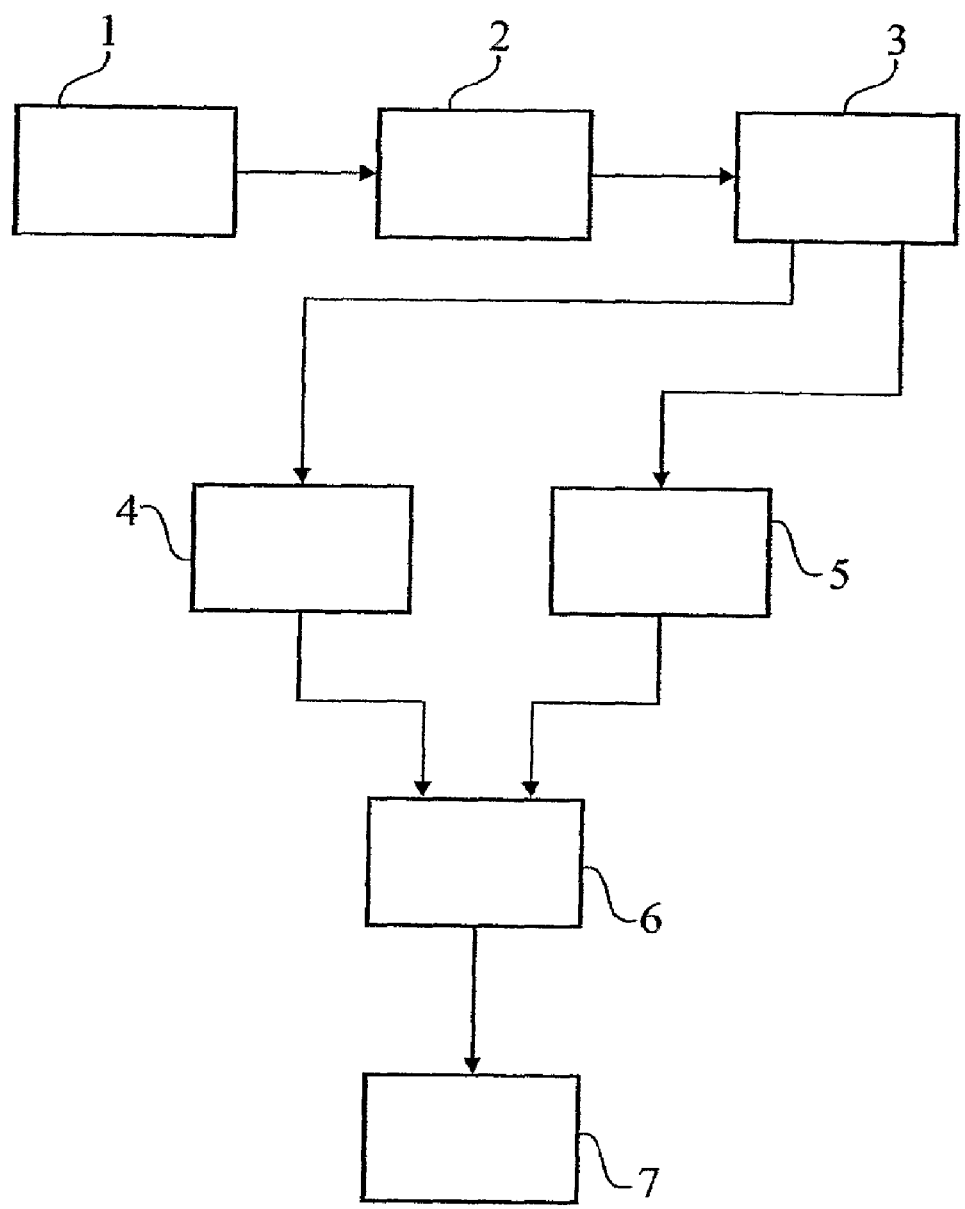
FIG. 1 is a schematic view of an embodiment of a system for manufacturing a dental component and a physical dental model.

FIG. 1 illustrates a system for manufacturing the dental component and the physical dental model 80 according to an embodiment. The system comprises an impression taking member 1, a scanner device 2, a data record generating unit 3, a first manufacturing device 4, a second manufacturing device 5, a fitting equipment 6, and installation equipment 7.

Figure 2:
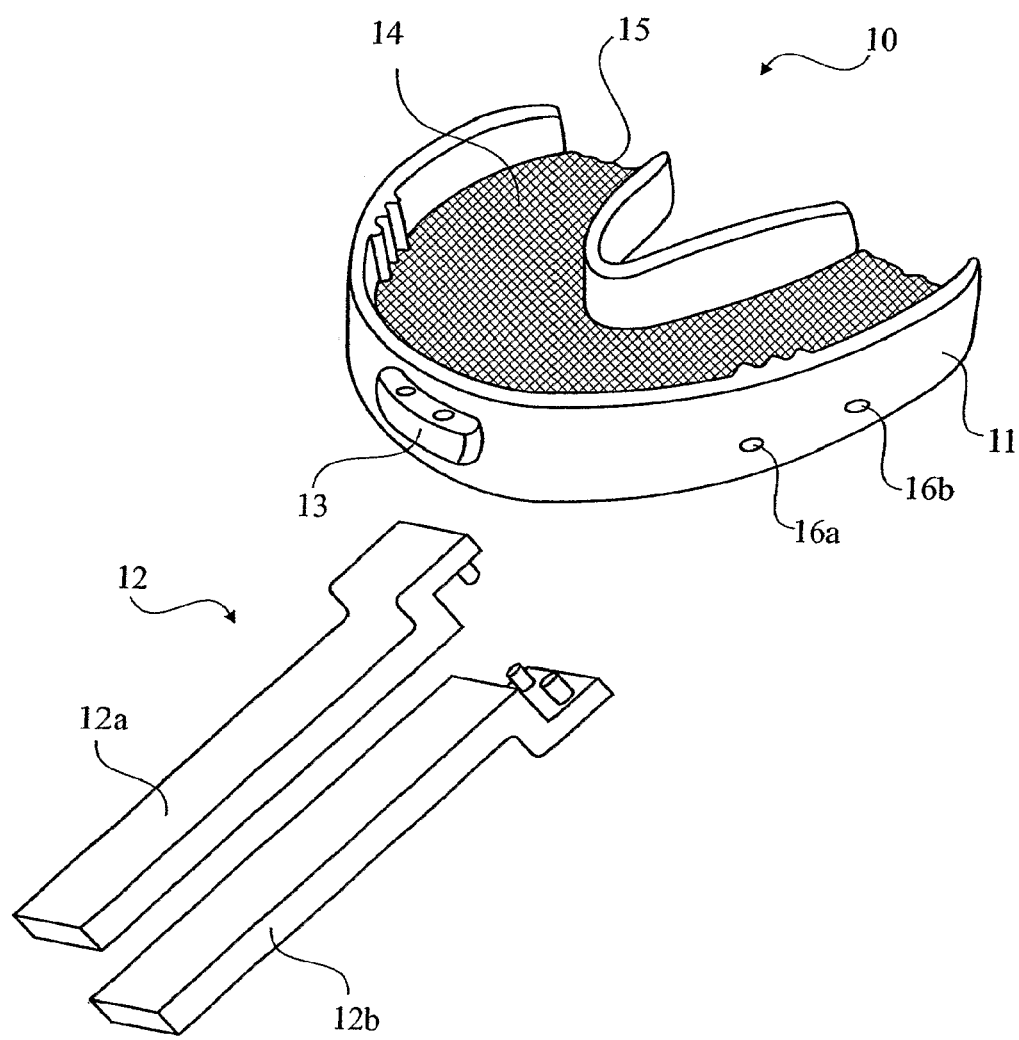
FIG. 2 is a perspective view of an embodiment of an impression tray.

FIG. 2 illustrates one embodiment of the impression taking member 2. In the embodiment of FIG. 2, the impression taking member comprises an impression tray 10, in which impression material may be applied. Embodiments of the impression tray 10 are designed for the system according to embodiments of the inventions. The impression tray 10 according to the embodiment of FIG. 2 is a triple impression tray, which may be used to obtain a physical impression 30 (FIG. 3b) of at least a part of an upper jaw, at least a part of a lower jaw, and a bite index in a single step when a patient bites the impression material. The embodiment of the impression taking member 1 as shown in FIG. 2 is the subject of a separate patent application titled "A Dental Impression Tray for use in Obtaining an Impression of a Dental Structure," PCT Application No. PCT/SE2007/000925, filed on Jan. 8, 2007, claiming priority to Swedish Patent Application No. 0602272-7, filed on Oct. 27, 2006 by the Applicant of the present application, and which is incorporated herein in its entirety by reference.

The impression tray 10 comprises a tray portion 11 adapted to be loaded with impression material. The tray portion 11 is contoured to fit over at least a part of the dental structure (see FIG. 3b). The impression tray 10 further comprises a handle 12 connected to the tray portion 11 or adapted/shaped to be connected to the tray portion 11. The handle 12 has a first end at which the handle 12 is connected to the tray portion 11 or adapted to be connected to the tray portion 11. The handle 12 also has a second end that is a distal end in relation to the tray portion when the handle is connected to the tray portion.

In some embodiments, the second end of the handle 12 has an edge facing away from the tray portion. In such embodiments, the edge may form a visible straight line when it is seen from the side facing away from the tray portion. The straight line has a length of at least 30 mm. In some embodiments, the straight line that is formed by the edge when seen from the side facing away from the tray portion has a length of at least 60 mm. In some embodiments, the straight line formed by the edge may have a length of at least 80mm.

In some embodiments, the handle may be removably secured to the tray portion. In some embodiments, the handle 12 may comprise two separate handle parts 12a, 12b that are adapted to be connected to each other such that the separate handle parts 12a, 12b overlap each other partially, but not completely. In such embodiments where the handle comprises separate parts, the separate handle parts 12a, 12b may be adapted to be connected to each other by a snap-on catch formed by the handle parts 12a, 12b. However, the connection could also be something else than a snap-on connection.

In embodiments where the handle comprises separate parts, the separate parts 12a, 12b may be identical in shape. Embodiments are also possible where separate handle parts are not identical in shape. In embodiments where the handle 12 comprises separate handle parts 12a, 12b, each of the separate handle parts 12a, 12b may be designed to cooperate with a complementary part 13 of the tray portion 11 in such a way that the handle 12 is locked to the tray portion 11 as long as the separate handle parts 12a, 12b are connected to each other.

The tray portion 11 has a shape that defines at least one cavity 14 with an inner wall 15. In some embodiments, the impression tray 10 may also comprise a pad that fits into at least a part of the cavity 14 of the tray portion 11. In such embodiments, the inner wall 15 may possibly be provided with a first guide structure and the pad may be provided with a second guide structure that fits the first guide structure. Thereby, the first and second guide structures may cooperate with each other in a way that permits the pad to move in the tray portion in a movement guided by the cooperating guide structures. The first guide structure may comprise projecting parts forming rails and the second guide structure comprises grooves adapted to receive the projecting parts of the first guide structure. An alternative possibility could be, for example, that the second guide structure comprises rails that interact with grooves in the inner wall 15.

The pad can be made of many different materials. In some embodiments, the pad is made of an elastic material.

In some embodiments, the tray portion 11 may be contoured to fit over a part of both the upper and lower dentition of a patient (see FIG. 3a) and an outer surface of the impression tray 10 may be provided with at least one fiduciary marker 16a, 16b that can be detected in a scanning operation. Such a fiduciary marker 16a, 16b can take many different shapes and may be formed in many different ways. In some embodiments, such a fiduciary marker 16a, 16b can be made in a material that is opaque to radio waves. This can be useful to use the impression tray 10 as a radiographic guide.

In some embodiments, the impression tray 10 may be provided with a machine-readable marking such as, for example, an RFID tag. The machine-readable marking could also be accomplished in other ways, for example, as a bar code. The identifier of the machine-readable marking can be inputted into at least one of the first data record and the second data record.

In the following, reference will also be made to a physical impression 30. The physical impression 30 may comprise an impression of at least a part of a dental structure of the patient. The dental structure may comprise at least one tooth, at least one preparation, and/or soft tissue. Each preparation may comprise a single tooth or several teeth. The preparation may comprise one tooth on which a dental crown, an inlay, or an onlay is to be mounted. Alternatively or additionally, the preparation may comprise several teeth on which a dental bridge is to be mounted.

Figure 3A:
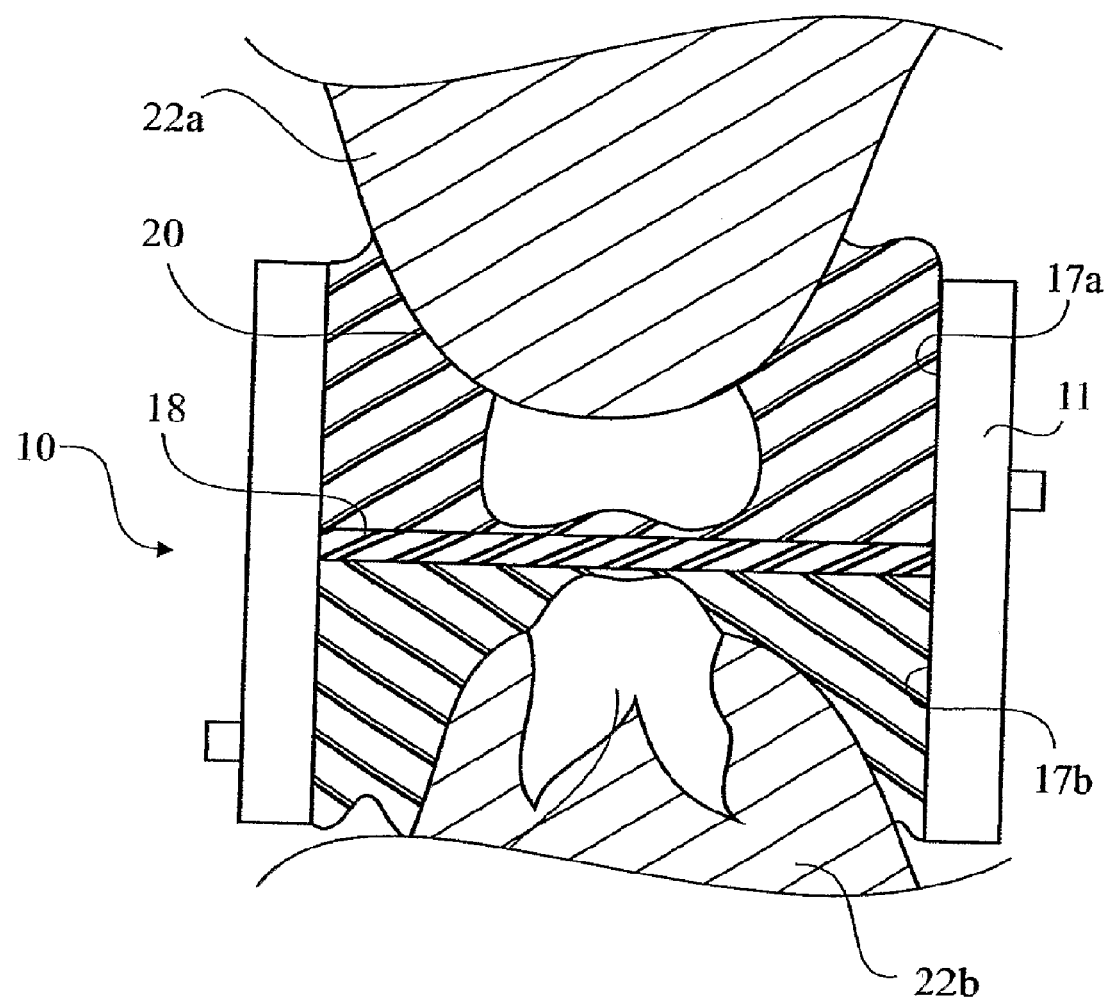
FIG. 3a is a cross-sectional view of the impression tray of FIG. 2 when a patient bites in impression material.

FIG. 3a discloses a cross section of the impression tray 10 of FIG. 2. A first cavity 17a and a second cavity 17b of the impression tray 10 are filled with impression material. The first cavity 17a and the second cavity 17b are separated by a partition 18. In the embodiment of FIG. 3a, a patient bites the impression tray 10 to make the physical impression 30. A first tooth 20 has entered the first cavity 17a. A preparation 21 has entered the second cavity 17b. Soft tissue 22a, 22b has entered both the first cavity 17a, and the second cavity 17b. When the impression material has set, the impression tray 10 can be removed from the patient and the impression material with the physical impression 30 formed therein will remain in the impression tray 10.

Figure 3B:
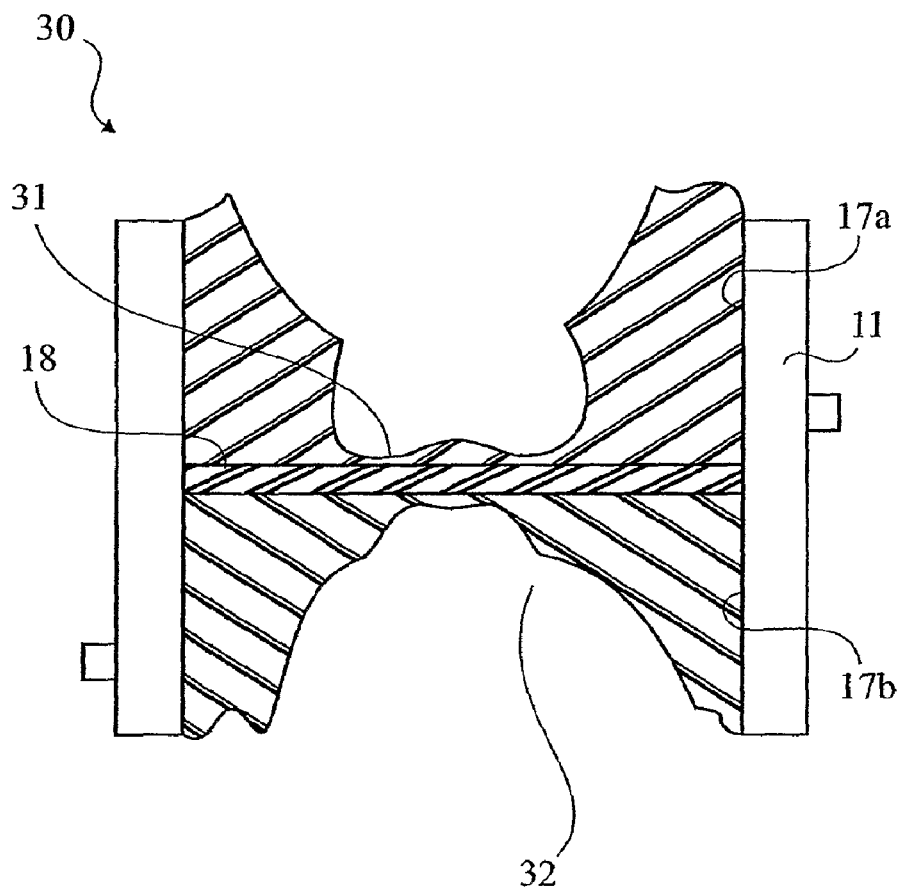
FIG. 3b is a cross sectional view of the impression tray of FIG. 2 with a physical impression.

FIG. 3b illustrates the physical impression 30. In the embodiment of FIG. 3b, the physical impression 30 comprises a first physical impression 31 and a second physical impression 32. The first physical impression 31 comprises an impression of the tooth 20 and the soft tissue 22a. The second physical impression 32 comprises an impression of the preparation 21 and the soft tissue 22b.

Figure 4:
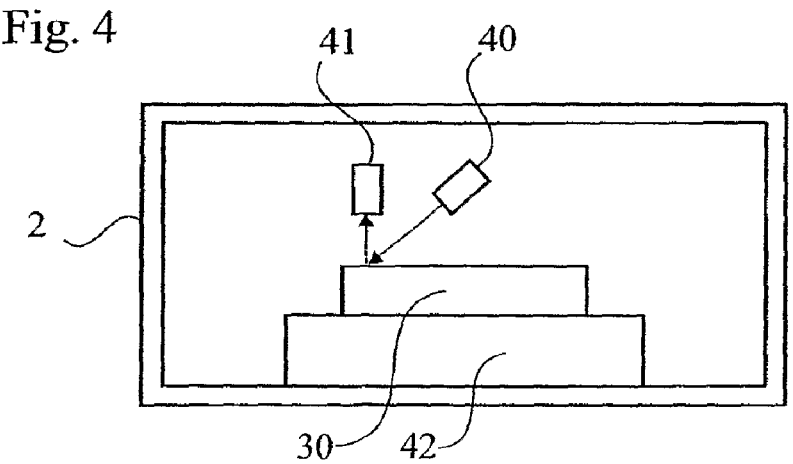
FIG. 4 is a schematic view of an embodiment of a scanner device.
Figure 5:
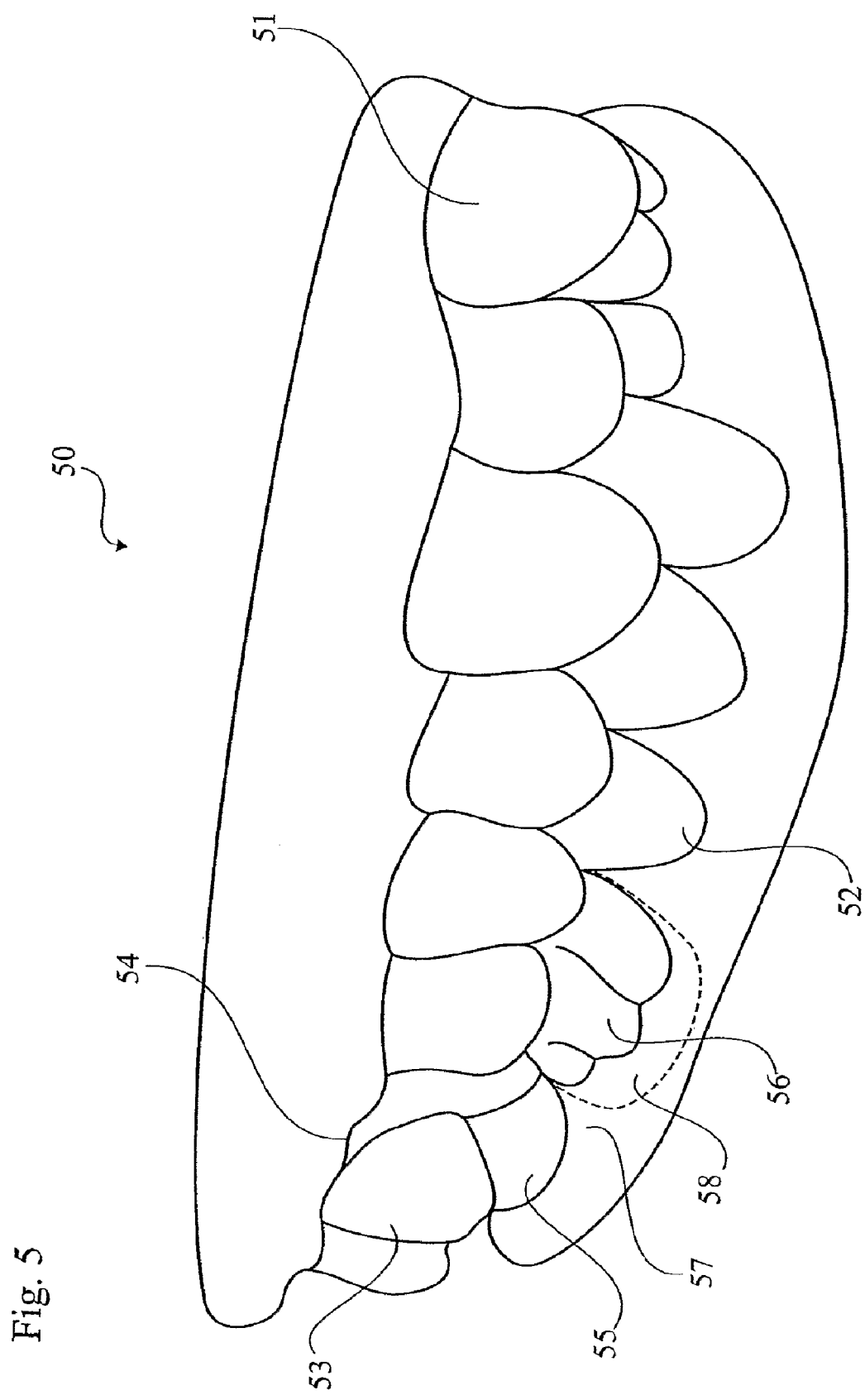
FIG. 5 is a perspective view of an embodiment of a digital dental model.

The scanner device 2 may be used for generating data for a digital dental model 50 of the physical impression 30. An embodiment of the scanner is shown in FIG. 4, and an embodiment of the digital dental model 50 is shown in FIG. 5. The data for the digital dental model 50 may be surface data, which reproduces the geometrical shape of the dental structure of the patient. The surface data may be, e.g., 3-D (three dimensional) vector based surface data.

In one embodiment, the scanner device 2 comprises an optical scanner, such as a laser scanner. Software may be used to control the scanner device 2 according to embodiments of the method according to the inventions. The scanner device 2 may operate on the physical impression 30. An optical scanner that operates on a physical impression 30 is available from the company 3Shape, Denmark, under the trade name D-250™. In some embodiments, the optical scanner is a laser line scanner. In other embodiments, the optical scanner is a laser scanner utilizing laser triangulation.

As noted above, FIG. 4 illustrates an embodiment of the scanner device 2. The scanner device 2 of FIG. 4 comprises a light transmitter 40 and a light receiver 41. Light emitted by the light transmitter 40 may be reflected by the physical impression 30 and received by the light receiver 41. Furthermore, the scanner device 2 comprises a moveable plate 42. The physical impression 30 may be positioned on the moveable plate 42 and moved during scanning such that the physical impression 30 is visible for the light transmitter 40 and the light receiver 41.

In another embodiment, the scanner device 2 comprises an intra-oral scanner device for impression-less scanning. One example of an intra-oral scanner is available from the company Cadent INC., Carlstadt, N.J., USA. Thus, according to some embodiments, impression-less generation of a dental component and the physical dental model 30 is provided for.

As noted above, FIG. 5 illustrates an embodiment of a digital dental model 50. The digital dental model 50 may comprise a first digital dental model 51 and a second digital dental model 52. The first digital dental model 51 may be a model of an upper jaw. Also, the first digital dental model 51 may include at least one tooth 53, at least one preparation (not shown), and/or soft tissue 54. The second digital dental model 52 may be a model of a lower jaw. Also, the second digital dental model 52 may include at least one tooth 55, at least one preparation 56, and/or soft tissue 57. The first digital dental model 51 and the second digital dental model 52 may be models of occluding portions of the dental structure of the patient, such as a preparation and its antagonist.

Figure 6:
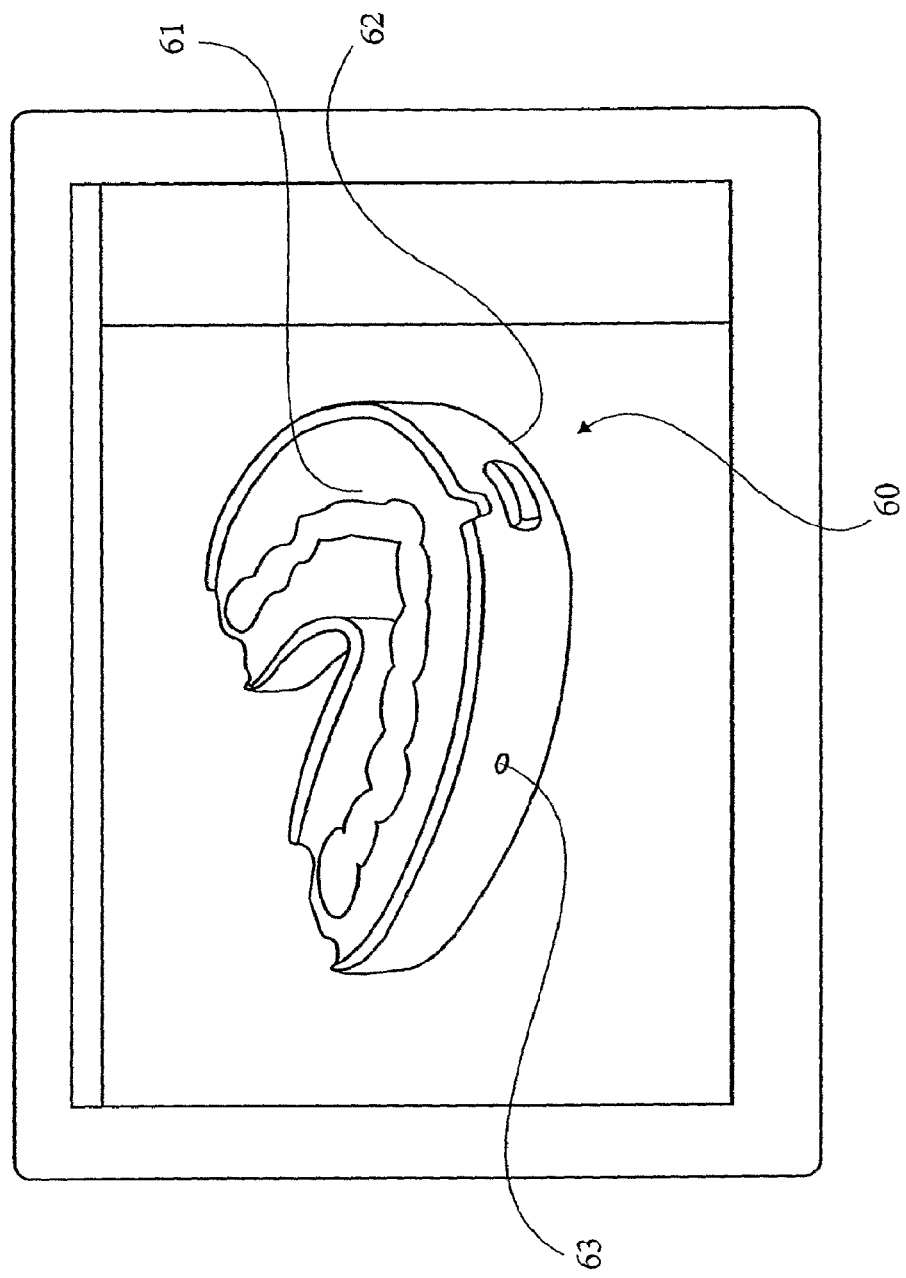
FIG. 6 is a perspective view of an embodiment of a digital dental impression.

FIG. 6 illustrates a digital impression 60. The digital impression 60 comprises at least one digital impression of the oral structure. In the embodiment of FIG. 6, the digital impression 60 comprises a first digital impression 61 and a second digital impression 62. Furthermore, in the embodiment of FIG. 6, the first digital impression 61 and the second digital impression 62 are impressions of occluding portions of the dental structure.

Figure 7:
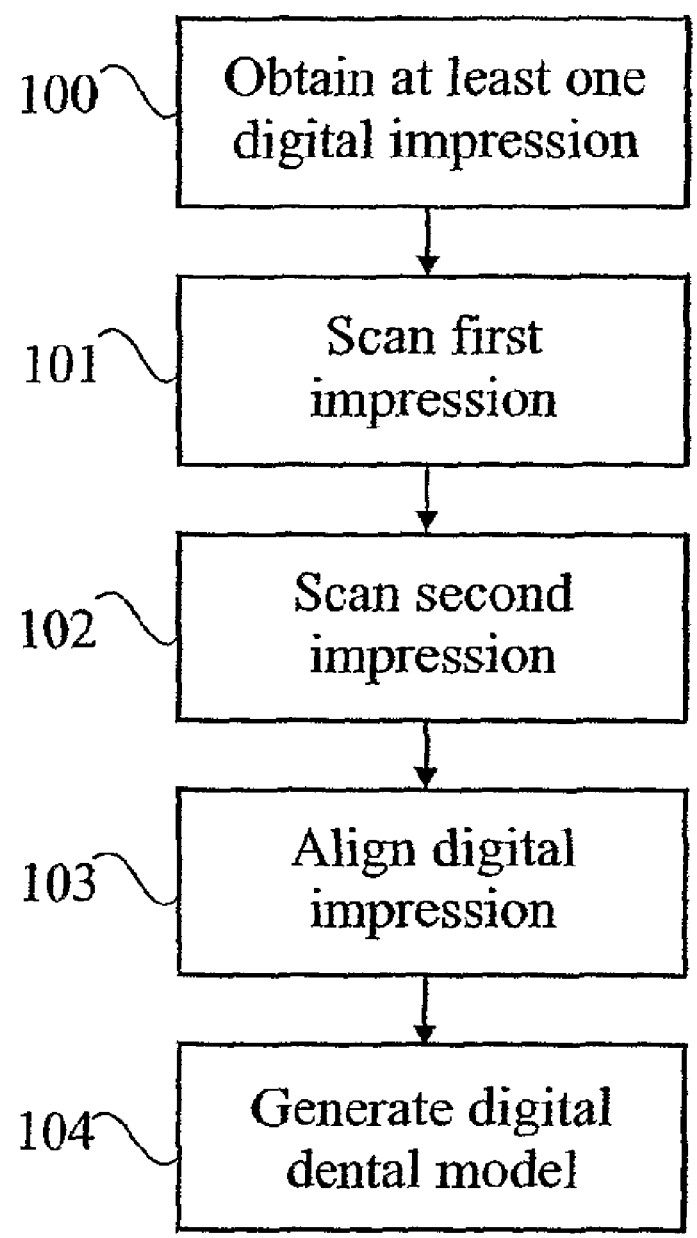
FIG. 7 is a flow chart of an embodiment of the method for obtaining the first and the second data record.

FIG. 7 illustrates an embodiment of a method for obtaining the digital dental model 50. In a first step 100, at least one digital impression 60 is obtained. In one embodiment, the first digital impression 61 corresponding to a first portion of the first physical impression 31 is obtained. Furthermore, at least the second digital impression 62 corresponding to a second portion of the second physical impression 32 is obtained. The second digital impression 62 may be obtained if the physical model 60 should include adjacent and/or occluding portions of the dental structure. The first digital impression 61 comprises at least a digital impression of the preparation of the dental structure. Also, the first digital impression 61 may comprise a digital impression of at least one adjacent teeth and/or soft tissue. The second digital impression 62 may comprise digital impressions of at least one occluding teeth and/or soft tissue. Each occluding tooth or teeth of the second digital impression 62 may occlude the preparation, and/or a tooth or teeth of the first digital impression 61. The first digital impression 51 and the second digital impression 62 may be obtained by controlling the scanner device 2 to scan the physical impression 30.

Controlling the scanner device 2 may comprise controlling the light transmitter 40 and/or the light receiver 41. Controlling of the light transmitter 41 may comprise, e.g., directing the light transmitter/receiver 41, 42 towards the surface of the physical impression 30, controlling light generation and/or moving the physical impression 30 relative the light transmitter/receiver 41, 42, or vice versa. Alternatively, movement of the light transmitter/receiver 41, 42 and/or the physical impression 30 are controlled. Communication with the scanner device 2 may also be controlled such that data obtained by the scanning operation is received by the data record generating unit 3 from the scanner device 2. Controlling the scanner device 2 comprises in some embodiments controlling the scanner device 2 to perform a measurement method. The measurement method comprises measuring a distance from a point of reference to the surface of the physical impression 30. The measurement method also comprises obtaining the geometrical shape of the physical impression 30 based on the measurement data and to form a digital impression 60 therefrom.

Generating the first digital impression 61 and the second digital impression 62 may be, e.g., used for manufacturing occluding portions of the physical dental model 80. The physical dental model 80 thus obtained may be used for at least one of occlusion checking and accuracy control of the dental component and/or the dental restoration. To provide the correct occlusional relationship between the first digital impression 61 and the second digital impression 62, the impression tray 10 according to FIG. 2 may be used.

According to some embodiments, the physical impressions 31, 32 are held by the impression tray 10 when the physical impressions 31, 32 are scanned. Then, the scanner device 2 can be controlled to scan the physical impressions 31, 32 as well as the impression tray 10. The first physical impression 31 together with at least a portion of the impression tray 10 is scanned in step 101. The second physical impression 32, together with the portion of the impression tray 10, is scanned in step 102. The first physical impression 31 and the second physical impression 32 may be scanned simultaneously or in subsequent steps. Scanning in subsequent steps provides for using a single light transmitter/receiver pair. The portion of the impression tray being scanned in step 101 is the same as the portion of the impression tray being scanned in step 102. The portion of the impression tray being scanned may comprise at least a portion of an exterior surface of the impression tray 10, which is not covered by impression material. The portion of the impression tray being scanned may comprise at least one of the fiduciary markers 16a, 16b.

Based on the scanning data obtained in steps 101 and 102, the first digital impression 61 and the second digital impression 62 may be obtained. The first digital impression 61 and the second digital impression 62 comprise a digitized version of the portion of the impression tray being scanned. In FIG. 6, the digitized version of the portion of the impression tray being scanned comprises a fiduciary marker 63.

In step 103, the first digital impression 61 is aligned with the second digital impression 62. The first digital impression 61 and the second digital impression 62 may be aligned by aligning at least a portion of the digitized version of the portion of the impression. The more of the digitized version of the impression tray being aligned, the better the aligning may be. Correct occlusional relationship between the first digital impression 61 and the second digital impression 62 will be provided, as the digitized version of the portion of the impression tray 10 in each digital impression 61, 62 has the same origin. Hence, the spatial relationship between the first and the second digital impressions 61, 62 will correspond to the spatial relationship between the dental structure, on which the first and second impressions 61, 62 are based.

In some embodiments, the aligning operation may comprise adding a digital marker on the fiduciary marker 63 of the first digital impression 61 and a second digital marker on the same fiduciary marker 63 of the second digital impression 62. The digital markers may be added manually by an operator by placing the marker by controlling, e.g., the cursor. The digital markers may indicate an area of the portion of the digitized version of the impression tray, at which the aligning operation should commence. This may decrease the processing time of the aligning operation. The aligning operation per se may be carried out by image processing, as is generally known. A process for aligning digital impressions is, e.g., available for said dental scanner D-250™.

In some embodiments, the scanner device 2 is controlled to apply a first scanning resolution for a first portion of the physical impression 30 and a second scanning resolution for a second portion of the physical impression 30. The first scanning resolution may be higher than the second scanning resolution. The portion being scanned using the first scanning resolution may be the physical impression of the preparation portion of the dental structure. The portion being scanned using the second scanning resolution may be the impression of the preparation portion. Furthermore, at least a portion of the dental structure being adjacent to the preparation portion may be scanned using the second scanning resolution. The adjacent portion may be, e.g., one or several teeth adjacent the preparation portion, teeth occluding the preparation portion and/or the adjacent tooth or teeth, and/or soft tissue. After scanning using the first and the second resolutions has been made, the data obtained using the first scanning resolution is merged or combined with the data obtained using the second scanning resolution. A process for merging the data is available for said dental scanner D-250™.

In some embodiments, a single scanning resolution is used. The first scanning resolution may be set to be high enough for providing sufficient resolution of the digital dental model 50 for manufacturing the restorative dental model. The second scanning resolution may be high enough for manufacturing the physical dental model 80. The requirement of the accuracy for the dental component is normally higher than the accuracy for the physical dental model 80. Thus, only the portion of the digital dental model 50 on which the dental component will be based needs to be obtained using the first scanning resolution. Utilizing a higher scanning resolution compared to a lower scanning resolution normally increases processing time. Therefore, utilizing the first and the second scanning resolution decreases the total processing time, albeit with sufficient accuracy for the restorative dental restoration as well as the physical dental model 80.

The scanning resolution may be set using the following procedure. First, the scanner is controlled to obtain test data of at least the physical impression 30 and possibly of the impression tray 10. The test data may be provided using a scanning resolution being lower than the first scanning resolution. The test data is visualized such that the user knows that the physical impression 30 and the impression tray 10 are scannable, i.e. visible for the light transmitter 40 and the light receiver 41. Also, the user may select the portions of the physical impression 30 that are to be scanned using the first and the second scanning resolutions. The portions may be selected by controlling the cursor and drawing a reference line around the portions to be scanned using the first and the second scanning resolutions. Then, the scanning operation can commence. The scanning using the first and the second scanning resolutions can be made automatically. By selecting the areas to be scanned, any area that is undesirable to be scanned will be omitted during the scanning process. Hence, the scanning time for scanning the object in the scanner device 2 compared to scanning the entire object in the scanner device 2 can be decreased.

In FIG. 5, a reference line 58 indicates an area that has been scanned using the first scanning resolution. The area inside the reference line forms a preparation portion of the second digital impression 62. The preparation portion may comprise the preparation 56 as well as the soft tissue 57.

The digital impression 60 may be, e.g., represented as a point cloud. Positive digital dental models may be generated based on the digital impressions 61, 62 in step 104. Converting a negative geometrical shape to its corresponding positive geometrical shape is generally known. A process for this purpose is e.g. available for said dental scanner D-250™. Hence, converting the digital impression 6+ into a positive dental model will not be discussed in any further detail herein. In some embodiments, the digital dental impressions 61, 62 are converted into digital dental models 51, 52 before the aligning operation. Thus, the first digital dental model 51 and the second digital dental model 52 are aligned using the same procedure as for aligning the first digital impression 61 and the second digital impression 62. A process for aligning the first digital impression 61 and the second digital impression 62 is also available from 3Shape for said dental scanner D-250™. According to some embodiments, a first data record and a second data record are obtained. The first data record and the second data record may be obtained from a single digital dental model 50. The digital dental model 50 comprises at least the preparation 56 for which the dental component is intended.

The first data record comprises information based on the preparation portion of the digital dental model 50. The first digital record may be used for manufacturing the dental component.

The second data record comprises information based on at least a portion of the digital dental model 60. The portion is at least the portion on which the first data record is based. The portion may comprise the digital preparation 56. Furthermore, the information of the second data record may be based on any other portion of the first digital dental model 51 and/or the second digital dental model 52. The second data record may be used for manufacturing the physical dental model 80. In some embodiments, the second data record only comprises information based on the digital preparation 56, and possibly soft tissue 57, but no adjacent tooth or teeth.

Obtaining the second data record may comprise adding a connection interface to the digital dental model 50. Information of the connection interface is included in the second data record. The connection interface of the physical dental model 80 may be used to connect the physical dental model 80 to the fitting equipment 6. In another embodiment, the connection interface and the fitting equipment are provided as an integral unit. Thus, also digital fitting equipment may be added to the digital dental model 50 and information based on the digital fitting equipment included into the second data record. This provides for generating customized fitting equipment. The digital fitting equipment may be, e.g., a digital articulator.

The first digital dental model 51 and the second digital dental model 52 may be related to a virtual reference plane. In some embodiments, the connection interface for the first digital dental model 51 may have a first spatial relationship relative the virtual reference plane. The connection interface for the second digital dental model 52 may have a second spatial relationship relative the reference plane. In some embodiments, the digital dental models 51, 52 are aligned with the virtual reference plane. Hence, the digital dental models 51, 52 are aligned with the connection interfaces. The second record may comprise information of at least one of a first surface and a second surface. The first surface may be formed by at least portion of the first digital dental model 51 and its associated connection interface. The second surface may be formed by at least a portion of the second digital dental model 52 and its associated connection interface. The information of the first surface and the information of the second surface may comprise the geometrical shape of first surface and the second surface, respectively. The information of the first surface and the information of the second surface may be vector based CAD information, such as a 3D shape.

Generation of data for the dental component can be carried out by a data generating process adapted therefore. The data generating process may be, e.g., provided by a CAD application.

In the following, an embodiment of a data generating process adapted for generating data for the first data record will be described. The preparation 56 of the digital model 50, i.e. the digital preparation 56, may be generated by removing a portion from the digital dental model 50. In some embodiments, the digital preparation 56 is generated by marking a certain area of the digital dental model 50, e.g., by controlling a cursor of the CAD application. The area marked can be copied. Alternatively, the area marked can be cut out. Furthermore, at least the digital preparation 56 of the preparation portion could be represented in the first scanning resolution. Thus, any dental component manufactured on the basis of the digital preparation 56, which in turn is based on the digital dental model 50, may have an accuracy corresponding to the scanning resolution, albeit depending on the manufacturing accuracy. The digital preparation 56 may form basis for manufacturing the dental component.

A digital preparation line may be added to the preparation portion. The digital preparation line may be used to define where the dental component should end. The geometry of the surface of the dental component may correspond to the geometry of the digital preparation 56 as delimited by the preparation line. The preparation line may be used to define a coping. If the preparation comprises a first and a second preparation portion, the preparation portions may be used so as to form a dental bridge coping. In some embodiments, the digital preparation is formed by a plurality of line markers. The preparation line is formed by connecting the line markers with a line. The line markers may be positioned by controlling a cursor, and/or using a drag-and-drop functionality of the CAD application.

The first manufacturing device A may operate based on a TRM file, i.e. a data file having the TRM file format. Furthermore, the digital preparation 56 may be represented by a surface model, such as data representing a vector based 3D model. The vector-based model may be converted to a TRM based representation. The conversion may be provided by scanning the surface of the preparation portion when it is in the vector-based representation. A virtual radial scanner may be utilized to provide data for the TRM file. The preparation line provides a line at which the scanning should end or commence. The data of the TRM file comprises a radial trace of coordinates, which together form a virtual surface, such as a 3D surface. Hence, a TRM file represents a 3D object using radial point information. In some embodiments, the virtual scanner measures the distance from a reference point to a specific point on the surface of the digital preparation 50. This may be, e.g., used to simulate a probe scanner.

When the digital preparation 56 has been scanned using the virtual scanner, the digital preparation 56 is represented by a first data set and a second data set. The first data set may be a vector-based representation. The second data set may be a point-based representation. In some embodiments, the first data set and the second data set are visualized simultaneously. Alternatively or additionally, the first data set is visualized superimposed over the second data set, or vice versa. Also, the first and second data sets may be visualized using a first and a second color. Hence, it is possible to visually verify that the first data set corresponds to the second data set in terms of their surface geometry. The outer data set may be visualized translucent, whereby it will be easier to verify the correspondence. Alternatively, the first and second data set may be visualized alternately one over the other.

By visualizing the first data set and the second data set, it may be visually determined whether an surface formed by the first data set corresponds to an surface formed by the second data set.

The first data record may comprise information, such as a first data file, which includes data describing the geometrical shape of the dental component to be manufactured. A first file format may be used for the first data file. The first file format may correspond to the file format used by the first manufacturing device 4. Furthermore, the first file format may be, e.g., the TRM file format.

The first data record and/or the second data record may comprise patient information. The patient information may be, e.g., identification data. The identification data may be a user-selected identifier. Alternatively or additionally, the identification data may be a unique identifier, such as a UUID (Universally Unique Identifier). The patient information may also comprise name, treatment ID, and/or patient number. The identification data may also be identification data of the impression tray 10.

The second data record may comprise information, such as at least a second data file, which includes data describing the geometrical shape of the physical dental model 80 to be manufactured. The second data record may comprise separate data files for the first physical dental model 81 and the second physical dental model 82 to be manufactured. Alternatively, a single data file comprises data describing the geometrical shape of both the first and the second physical dental model 61, 62. A second file format may be used for the second data file. The second file format may correspond to the file format used by the second manufacturing device 5. The second file format may be, e.g., the STL (Stereo Lithography) file format.

In some embodiments, obtaining the first data record comprises receiving the first data record at the first manufacturing device 4. Also, obtaining the first data record may comprise retrieving the first data file from the first data record. Then, the first manufacturing device 4 may be controlled using the first data file. Controlling such a manufacturing device utilizing a data file describing a geometrical shape is generally known and will not be described in detail herein.

In some embodiments, obtaining the second data record comprises receiving the second data record at the second manufacturing device 5. Also, obtaining the second data record may comprise retrieving the second data file from the second data record. Then, the second manufacturing device 5 is controlled using the second data file.

The first manufacturing device 4 may comprise free form fabrication equipment. The free form fabrication equipment may comprise, e.g., a CIM (Computer Integrated Manufacturing) system. The CIM system may comprise, e.g., at least one of an SLA (Stereo Lithographic Apparatus), a CNC (Computer Numeric Controlled) machining, an EDM (Electro-Discharge Machining) and a Swiss Automatics machining system. For example, if a SLA system is used, the second file format may have the STL file format. Controlling such manufacturing device utilizing a data file describing a geometrical shape is generally known and will not be described in detail herein.

When the physical dental model 80 and the dental component have been manufactured, the fitting equipment 6 can be used to finalize the dental restoration. The fitting operation may comprise, e.g., veneering the dental component, grinding, and/or occlusion checking.

Figure 8:
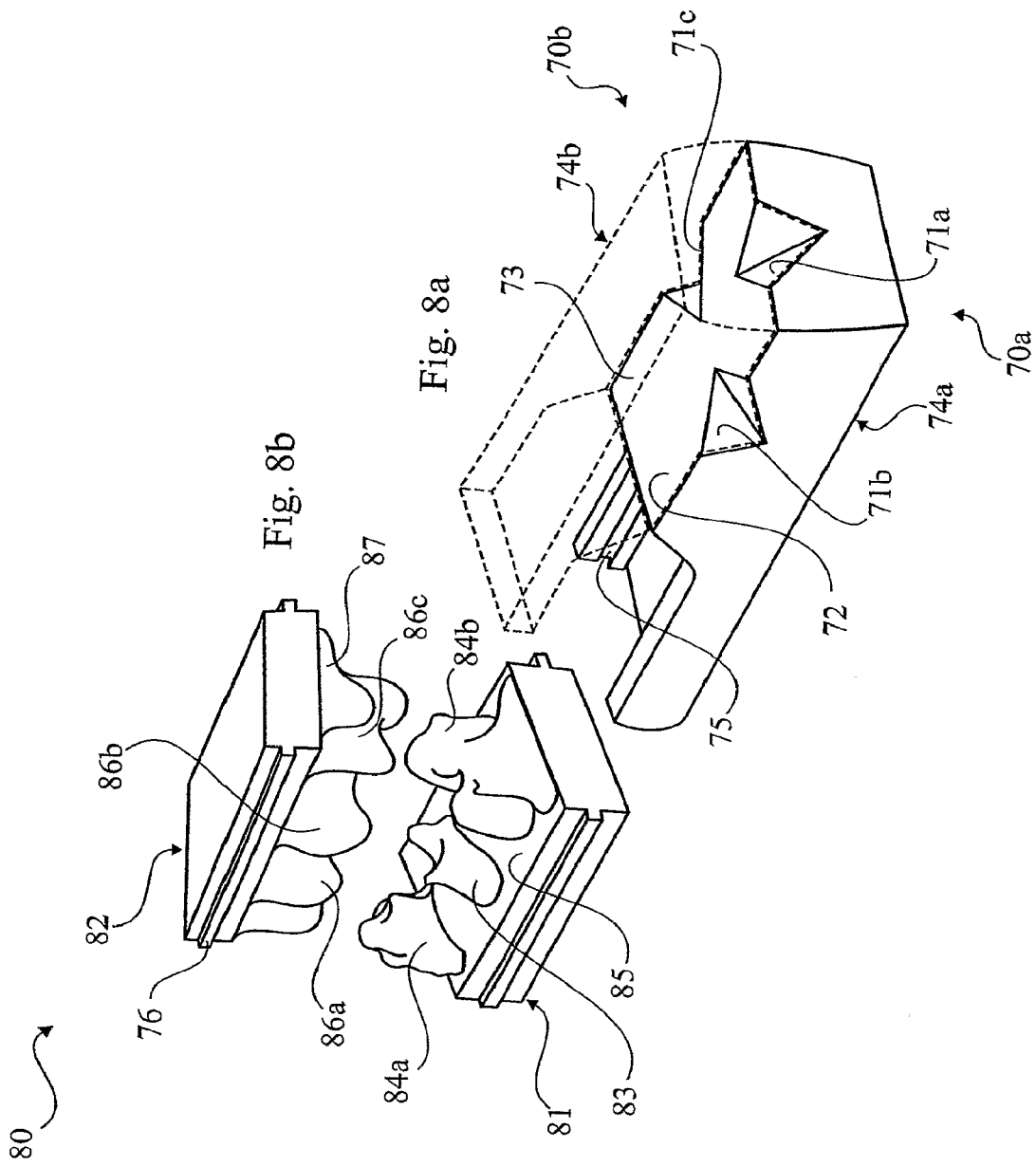
FIG. 8a is a perspective view of an embodiment of an articulator.
FIG. 8b is a perspective view of an embodiment of a physical model.

FIG. 8a illustrates one embodiment of the fitting equipment 6. The fitting equipment 6 and physical dental model 80 are also subject to a separate patent application titled "Dental Model, Articulator and Methods for Production Thereof," PCT Application No. PCT/SE2007/000922, filed on Oct. 18, 2007, claiming priority to Swedish Patent Application No. 0602273-5, filed Oct. 27, 2006 by the Applicant of the present application, and which is incorporated herein in its entirety by reference.

In the embodiment of FIG. 8a, the fitting equipment 6 comprises an articulator 70 designed for the system according to embodiments of the inventions. The articulator 6 comprises a first part 70a and a second part 70b. The second part 70b is shown with phantom lines for illustrative purposes. Each part comprises a male/female device. Each male/female device comprises at least two separate, discrete elements 71a, 71b. In some embodiments, the male/female device comprises three separate discrete elements 71a, 71b, 71c. The discrete elements 71a, 71b, 71c may be formed as a protrusion and a recess. The discrete elements 71a, 71b, 71c are provided for simulation of the natural movement of a jaw of a patient for a fitting operation and accuracy checking. The size and position of the discrete elements 71a, 71b, 71c are arranged to form a gap between sidewalls of each one of said protrusion and recesses, respectively, when surfaces 72, 73 are in contact. The surfaces 72, 73 are positioned on holding parts 74a, 74b of the first and the second part 70a, 70b of the articulator 70, respectively.

The articulator 70 comprises a connection interface for attaching the physical dental model 80 (FIG. 8b) to the articulator 70. In the embodiment of FIG. 8a, the connection interface comprises an engagement interface 75. The engagement interface 75 may comprise at least one of a protrusion and a recess. The engagement interface 75 of the articulator 70 is adapted to engage an engagement interface 76 (FIG. 8b) formed integral with the physical dental model 80. The shape of the engagement interface 75 of the articulator 70 is in this embodiment complementary to the shape of the engagement interface 76 of the physical dental model 80. The engagement interface 76 enables quick-lock and quick-release of the physical dental model 80. In the embodiment of FIGS. 8a-8b, the engagement interface 75 of the articulator 70 comprises an elongated recess. The engagement interface 76 of the physical dental model 80 comprises an elongated protrusion.

Hence, a slide engagement is facilitated. In other embodiments, the engagement interfaces 75, 76 form a snap-fit interface. A releasable engagement interface between the articulator 70 and the physical dental model 80 provides for making the articulator 70 reusable. Also, the material of the physical dental model 80 may be kept to a minimum.

In some embodiments, the physical dental model is integrated with the articulator (not shown). Then, the engagement interface of the articulator is integrally formed with the physical dental model. If the physical dental model is integrated with the articulator, exact and durable positioning of the physical dental model into the articulator is achieved. The positioning may also be made extremely strong, e.g., withstanding rough handling during transport.

FIG. 8*b* illustrates the physical dental model 80. The physical dental model 80 may comprise a first physical dental model 81 and a second physical dental model 82. The first physical dental model 81 may be a model of an upper jaw and may include at least one tooth, at least one preparation, and/or soft tissue. The second physical dental model 82 may be a model of a lower jaw and may include at least one tooth, at least one preparation, and/or soft tissue.

In the embodiment of FIG. 8*a*, the first physical dental model 81 comprises a model of the preparation 83. The first physical dental model 81 also comprises models of teeth 84*a*, 84*b* adjacent the preparation 83 and soft tissue 85. The second physical dental model 82 comprises models of occluding teeth 86*a*, 86*b*, 86*c* and soft tissue 87. In some embodiments, a third physical model is provided (not shown). On the third physical model, a recess is provided around the model of the preparation 83. The recess is provided at the position where the dental component will end when it is seated on the model of the preparation 83. This will simplify accuracy checking. The recess can be formed using the CAD application according to embodiments of the inventions and thus included in the second data record.

Consequently, the recess around the model of the restoration can be manufactured using the second manufacturing device 5.

The dental model is in some embodiments made of a controllably curable material, which provides for that high accuracy and quality may be achieved irrespective of variations in temperature and humidity. Such controllably curable material may be any material used in a free form fabrication technique, such as a rapid prototyping technique. For example, if a SLA process is used, the controllably curable material may comprise a photopolymer resin. Said resin may be cured by controlling the beam of an ultraviolet laser. With a controllably curable material is meant a material that may be cured using a control device, such as the data record generating unit 3.

Figure 9:
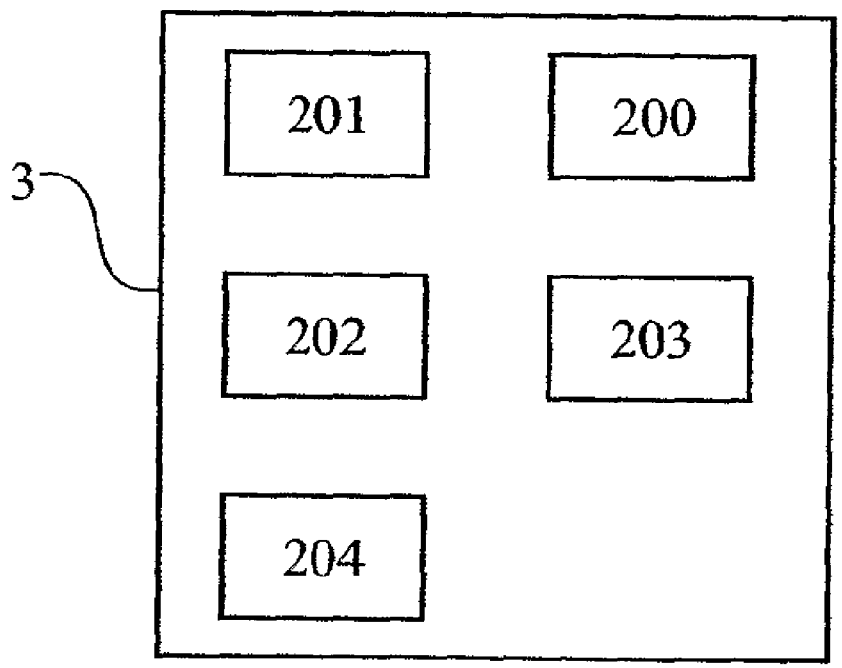
FIG. 9 is a schematic view of an embodiment of the data record generating unit.

FIG. 9 illustrates an embodiment of the data record generating unit 3. The data record generating unit 3 in the embodiment of FIG. 9 comprises a visualization unit 200, an input interface 201, a memory 202, a controller 203, and a communication interface 204. The data record generating unit 3 may comprise, e.g., a computer.

The visualization unit 200 may comprise a display. The visualization unit 200 may be used to display, e.g., the digital model 50, the digital impression 60, an application for the method according to embodiments of the inventions, and/or a CAD application.

The input interface 201 may comprise at least one of a mouse, a keyboard, a stylus pad, a touch pad, and a joystick. A user may input information into the data record generating unit 3 using the input interface 201. Furthermore, a user may control the cursor displayed on the visualization unit 200 using the input interface 201. The memory 202 may comprise at least one of a RAM (Random Access Memory), a ROM (Read Only Memory), a flash memory, and a non-volatile memory. The memory 202 may be used to store any information received from the scanner device 2. Furthermore, software for controlling the scanner device 2 and any other device or equipment may be stored in the memory 202. The memory 202 may also store software for performing the method according embodiments of the inventions.

The controller 203 may comprise a processing unit, such as at least one of a CPU (central Processing Unit) and an ASIC (Application Specific Integrated Circuit). The controller 203 may be adapted to run software for controlling the scanner device 2, communicate with the first manufacturing device 4 and/or the second manufacturing device 5 through the communication interface 204, and/or the carry out the method according to embodiments of the inventions.

The communication interface 204 may comprise at least one of a serial cable interface, a USB (Universal Serial Bus) interface, a WAN communication interface, and a LAN communication interface. Any of the scanner device 2, the first manufacturing device 4, and the second manufacturing device 5 may comprise a communication interface corresponding to the communication interface 204 of the data record generating unit 3.

The system according to the inventions can be located at one or several geographical locations. For example, the physical impression 30 may be generated at a first location, such as at a dentist. The scanner device 2 may be located at the first geographical location. Alternatively, the scanner device 2 may be located at a second geographical position, such as at a dental technician. The data record generating unit 3 may be located at the dentist, the dental technician or a manufacturing facility. The first manufacturing device 4 and the second manufacturing device 5 may be located at the same or different geographical locations. Any of the equipment of the system according to the inventions may be connected by a connection interface. Each connection interface may comprise a serial cable, a LAN (Local Area Network), and/or a WAN (Wide Area Network) connection interface.

After manufacturing of the physical dental model 30 and the dental component, they may be shipped to the geographical location of the fitting equipment 6, possibly via a distribution central. The geographical location of the fitting equipment 6 may be, e.g., a dentist or a dental technician. After the fitting operation, the dental restoration may be delivered for installation using the installation equipment 7. The installation equipment 7 may comprise cement for attaching the dental restoration to the preparation of the patient.

Providing information for manufacturing the dental component and the physical dental model 80 as data records provides for centralized manufacturing of a customized dental component as well as the physical dental model 80. This, in turn, provides for economics of scale, and thus reduced cost. The system according to embodiments of the inventions is flexible. Furthermore, the elimination of the plaster study cast provides for reduced number of steps that needs to be performed compared to utilizing plaster study casts.

For example, no sectionizing and/or grinding of the plaster study cast is needed. Hence, the efficiency of the system according to the inventions is improved compared to a system utilizing plaster study casts. The system according to embodiments of the inventions is also more efficient than any system utilizing manual fabricating, according to which the dental component is built up layer by layer based on a framework, even if the framework has not been fabricated by utilizing a plaster study cast. Manual fabrication of the dental component inherently involves a lot of work. As the dental component and the physical model 60 are based on a single digital model, and even the same surface of the digital model 50, superior accuracy may be provided. Hence, an inner surface of the dental component and an outer surface of the model can have a very close fit.

Embodiments of the inventions may be embedded in a computer program product, which enables implementation of the method and functions described herein. Embodiments of the inventions may be carried out when the computer program product is loaded and run in a system having computer capabilities. Computer program, software program, program product, or software, in the present context mean any expression, in any programming language, code or notation, of a set of instructions intended to cause a system having a processing capability to perform a particular function directly or after conversion to another language, code or notation. Each of the first data record and the second data record may be stored at a storage device. The first data record and the second data record may be stored at a common storage device. The common storage device may be, e.g., the memory 202 of the data record generating unit 3. Alternatively or additionally, the first data record and the second data record may be stored at separate storage devices. The separate storage devices may be, e.g., memories of each of the first manufacturing device 4 and the second manufacturing device 5, respectively.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

The invention claimed is:

1. A method for obtaining data for manufacturing a dental component and a physical dental model of at least a part of a dental structure, the method comprising:
obtaining a first data record for manufacturing the dental component, the first data record comprising information based on a portion of a digital dental model; and
obtaining a second data record for manufacturing the physical dental model, the second data record comprising information based on at least the portion of the digital dental model;
wherein obtaining the first data record comprises obtaining a data record comprising information, which is based on the portion of the digital dental model, said portion has been generated using a first scanning resolution; and
obtaining the second data record comprises obtaining a data record comprising information, which is based at on least the portion of the digital dental model said portion has been generated using a second scanning resolution the second scanning resolution being lower than the first scanning resolution.

2. The method according to claim 1, wherein obtaining the first data record comprises obtaining a data record comprising information based on a preparation portion of the digital dental model, and obtaining the second data record comprises obtaining information based on at least the preparation portion of the digital dental model.

3. The method according to claim 1, wherein obtaining the first data record and obtaining the second data record comprise obtaining information of a geometrical shape a surface of at least the portion of the digital dental model.

4. The method according to claim 1, wherein obtaining the second record comprises adding a connection interface to at least a portion of the digital dental model.

5. The method according to claim 1, wherein obtaining the first data record comprises receiving the first data record at a CAM apparatus, and manufacturing at least the dental component based on the first data record.

6. The method according to claim 1, wherein obtaining the second data record comprises receiving the second data record at a free form fabrication apparatus, and the method comprises manufacturing the physical dental model based on the second data record.

7. A computer program product comprising computer program code means for executing the method according to claim 1 when said computer program code means are run by an electronic device having computer capabilities.

8. A data storage device comprising at least one of the first data record and the second data record according to the method of claim 1.

9. A method for obtaining data for manufacturing a dental component and a physical dental model of at least a part of a dental structure, the method comprising:
obtaining a first data record for manufacturing the dental component the first data record comprising information based on a portion of a digital dental model; and
obtaining a second data record for manufacturing the physical dental model the second data record comprising information based on at least the portion of the digital dental model
obtaining at least one digital impression of a portion of a physical impression by controlling a scanner device, the portion of the physical impression comprising an impression of a portion of the dental structure; and
generating the dental model impression;
wherein the step of obtaining at least one digital impression comprises:
controlling the scanner device to apply a first scanning resolution when a first portion of the physical impression is scanned and to apply a second scanning resolution when a second portion of the physical impression is scanned, the first scanning resolution being higher than the second scanning resolution.

10. A system for obtaining data for manufacturing a dental component and a physical dental model of at least a part of a dental structure, said system comprising:
a data record generating unit adapted to obtain a first data record for manufacturing the dental component, the first data record comprising information based on a portion of a digital dental model; and obtain a second data record for manufacturing the physical dental model, the second data record comprising information based on at least the portion of the digital dental model;
wherein the data record generating unit is adapted to obtain for the first data record a data record comprising information, which is based on the portion of the digital dental model said portion has been generated using a first scanning resolution; and obtain for the second data record a data record comprising information, which is based at on least the portion of the digital dental model said portion has been generated using a second scanning resolution the second scanning resolution being lower than the first scanning resolution.

11. The system according to claim 10, wherein the data record generating unit is adapted to obtain for the first data record a data record comprising information based on a preparation portion of the digital dental model, and obtain for the second data record information based on at least the preparation portion of the digital dental model.

12. The system according to claim 10, wherein the data record generating unit is adapted to obtain for the first data record and the second data record information of a geometrical shape a surface of at least the portion of the digital dental model.

13. The system according to claim 10, wherein the data record generating unit is adapted to add a connection interface to at least a portion of the digital dental model.

14. The system according to claim 10, further comprising a CAM apparatus adapted to receive the first data record and manufacture at least the dental component based on the first data record.

15. The system according to claim 10, comprising a free form fabrication apparatus adapted to receive the second data record and manufacture at least the physical dental model based on the second data record.

16. A system for obtaining data for manufacturing a dental component and a physical dental model of at least a part of a dental structure, said system comprising;
- a data record generating unit adapted to obtain a first data record for manufacturing the dental component, the first data record comprising information based on a portion of a digital dental model; and obtain a second data record for manufacturing the physical dental model, the second data record comprising information based on at least the portion of the digital dental model;
- wherein the data record generating unit is adapted to obtaining at least one digital impression of a portion of a physical impression by controlling a scanner device, the first portion of the physical impression comprising an impression of a portion of the dental structure; and generate the digital dental model based on the digital impression; and
- wherein the data record generating unit is adapted to control the scanner device to apply a first scanning resolution when a first portion of the physical impression is scanned and apply a second scanning resolution when a second portion of the physical impression is scanned, the first scanning resolution being higher than the second scanning resolution.

* * * * *

UNITED STATES PATENT AND TRADEMARK OFFICE
CERTIFICATE OF CORRECTION

PATENT NO. : 8,234,000 B2  
APPLICATION NO. : 12/447467  
DATED : July 31, 2012  
INVENTOR(S) : Matts Andersson et al.

Page 1 of 1

It is certified that error appears in the above-identified patent and that said Letters Patent is hereby corrected as shown below:

In column 3, line 54, change "at on" to --on at--.
In column 4, line 50, change "at on" to --on at--.
In column 6, line 54, change "80mm." to --80 mm.--.
In column 9, line 41, change "occulsional" to --occlusional--.
In column 12, line 19, after "least" insert --a--.
In column 12, line 24, after "of" insert --the--.
In column 16, line 8, after "according" insert --to--.
In column 17, line 63, Claim 1, change "at on" to --on at--.
In column 17, line 64, Claim 1, change "model" to --model,--.
In column 17, line 65, Claim 1, change "resolution" to --resolution,--.
In column 18, line 34, Claim 9, change "component" to --component,--.
In column 18, line 37, Claim 9, change "model" to --model,--.
In column 18, line 39, Claim 9, change "model" to --model;--.
In column 18, line 44, Claim 9, after "the" insert --digital--.
In column 18, line 44, Claim 9, after "model" insert --based on the digital--.
In column 18, line 66, Claim 10, change "model" to --model,--.
In column 19, line 2, Claim 10, change "at on" to --on at--.
In column 19, line 2, Claim 10, change "model" to --model,--.
In column 19, line 4, Claim 10, change "resolution" to --resolution,--.
In column 20, line 3, Claim 16, change "comprising;" to --comprising:--.

Signed and Sealed this  
Second Day of April, 2013

Teresa Stanek Rea  
*Acting Director of the United States Patent and Trademark Office*